United States Patent [19]

Ison

[11] Patent Number: Plant 7,591

[45] Date of Patent: Jul. 16, 1991

[54] SUGARPOP

[76] Inventor: William G. Ison, Rte. 1, Box 19, Hwy. 19, Brooks, Ga. 30205

[21] Appl. No.: 166,246

[22] Filed: Mar. 10, 1988

[51] Int. Cl.[5] ..... A01H 5/00

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety Fry and the pollen parent variety 8-16-1 to produce an improved variety of self-fertile muscadine grape.

1 Drawing Sheet

DESCRIPTION OF THE VARIETY

A cross between the female bronze variety Fry and the pollen parent variety 8-16-1 which has not been released.

The primary objective of the breeding was to produce an improved variety of muscadine grape; the fruit of which would be large, bronze fresh fruit, with even ripening, high sugar content, dry scar for longer shelf life, high quality; and the plant to be productive and vigorous.

The new variety has a unique characteristic in that it pops open when you eat it. In comparison to the seed and pollen parents, the new variety is similar to both in size. The seed and pollen parents are similar to the new variety in color and sugar content. The fruit of this new variety contains an average of 21% soluble solids. The present variety is very productive; yielding 8 to 10 tons per acre in tests conducted at Ison's Nursery & Vineyards, Brooks, Ga. This fruit variety is mid to late season in ripening.

Asexual reproduction of the new variety either by soft-wood cuttings or by layering as performed at Brooks, Ga. shows that the foregoing characteristics and distinctions come true to form and are established and transmitted through succeeding propagations.

The accompanying photograph shows a typical specimen of the vegetative growth and fruit of the new variety when the fruit is ripe and ready for picking and as depicted in color as nearly true as it is reasonably possible to make the same in color illustration of the characters.

The following is a detailed description of the new variety:

Species: *Vitis rotundifolia.*
Type: Vine.
Seed parent: Variety Fry.
Pollen parent: Variety 8-16-1.

Propagation: Holds its characteristics through succeeding propagation by either layering or by soft-wood cuttings.
Locality where grown: Brooks, Ga.
Fruit:
- *Borne.*—Usually in clusters of 6 to 14 berries per cluster.
- *Size.*—Large, similar in size to the seed parent and the pollen parent, about 1⅛" diameter.
- *Color.*—Greyed Yellow group 161 A Fan 4 of The Royal Horticultural Society, London, England.
- *Sugar content.*—Average 21% soluble solids.
- *Shape.*—Round.
- *Seed.*—Average diameter ⅛ inch, average seed per berry 2.65.
- *Pulp.*—A. Color group, Greyed Green, 195B Fan 4 of The Royal Horticultural Society, London, England. B. Consistency of pulp meaty, soft and juicy when compared to most muscadine varieties.
- *Skin.*—Medium soft and edible.

Foliage:
- *Leaf color.*—Green Group 137 B Fan 3 The Royal Horticultural Society, London, England.
- *Leaf size and shape.*—Similar to most muscadine varieties.

Reproductive organs: Pistillate-not self pollinating. Note: this is a female variety which can be reproduced from cuttings but when planted will not pollinate other varieties.
Growth habits: Very vigorous and productive, high production being an outstanding characteristic; vine requires support.
Canes: Medium to large.
Maturity date: Usually ripens about October 1 at Brooks, Ga.
Diseases: Resistant to muscadine diseases.

This description was made from a muscadine vine grown at Ison's Nursery & Vineyards, Brooks, Ga.

I claim:

1. The new and distinct variety of grape plant as described and illustrated.

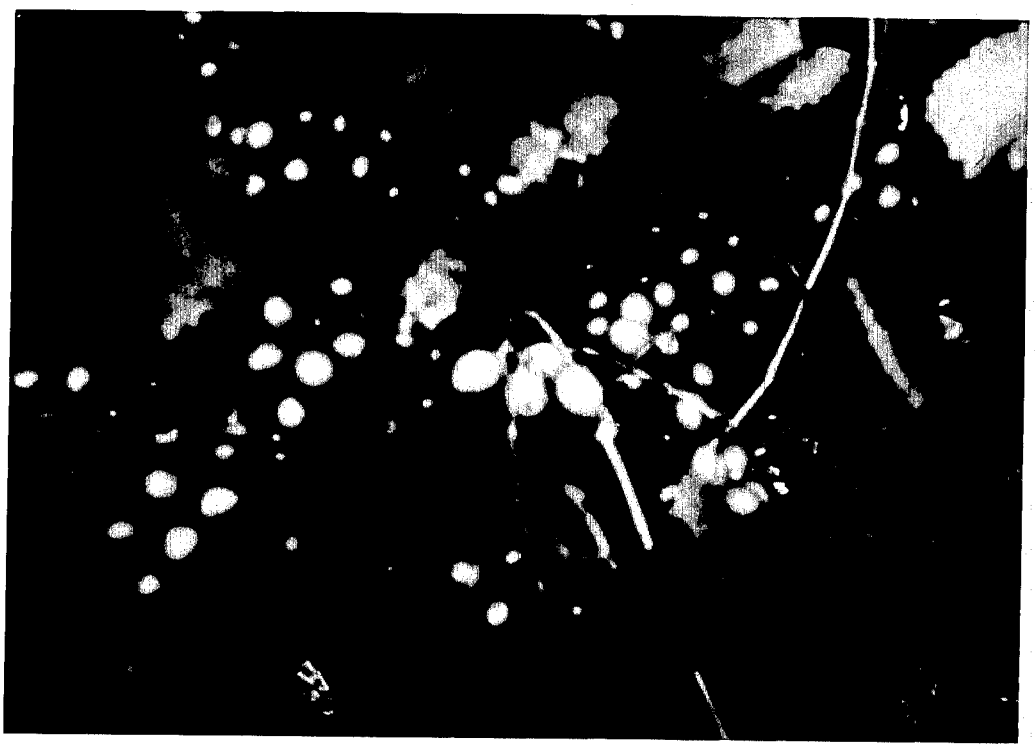

* * * * *